United States Patent [19]
Hendrickson et al.

[11] Patent Number: 5,286,497
[45] Date of Patent: Feb. 15, 1994

[54] DILTIAZEM FORMULATION

[75] Inventors: Dennis L. Hendrickson, Overland Park, Kans.; Dan C. Dimmitt, Belton; Mark S. Williams, Kansas City, both of Mo.; Paul F. Skultety, Leawood, Kans.; Michael J. Baltezor, Lees Summit, Mo.

[73] Assignee: Carderm Capital L.P., Thalwil, Switzerland

[21] Appl. No.: 58,534

[22] Filed: May 6, 1993

Related U.S. Application Data

[63] Continuation of Ser. No. 872,572, Apr. 23, 1992, abandoned, which is a continuation-in-part of Ser. No. 702,567, May 20, 1991, abandoned.

[51] Int. Cl.$^5$ .............................................. A61K 9/16
[52] U.S. Cl. ................................. 424/490; 424/489; 424/497
[58] Field of Search .................... 424/489, 490, 497

[56] References Cited

U.S. PATENT DOCUMENTS

| | | | |
|---|---|---|---|
| 4,871,731 | 10/1989 | Walker | 514/211 |
| 4,891,230 | 1/1990 | Geoghegan | 424/497 |
| 4,894,240 | 1/1990 | Geoghegan | 424/497 |
| 4,917,899 | 4/1990 | Geoghegan | 424/497 |
| 5,002,776 | 3/1991 | Geoghegan | 424/497 |
| 5,112,621 | 5/1992 | Stevens | 424/497 |
| 5,229,135 | 7/1993 | Philippon et al. | 424/494 |

FOREIGN PATENT DOCUMENTS

| | | |
|---|---|---|
| 193164 | 2/1986 | European Pat. Off. |
| 225085 | 11/1986 | European Pat. Off. |
| 282698 | 1/1988 | European Pat. Off. |
| 320097 | 10/1988 | European Pat. Off. |
| 315414 | 11/1988 | European Pat. Off. |
| 8802253 | 9/1987 | PCT Int'l Appl. |
| 9101722 | 7/1990 | PCT Int'l Appl. |

*Primary Examiner*—Thurman K. Page
*Assistant Examiner*—William E. Benston, Jr.
*Attorney, Agent, or Firm*—Killworth, Gottman, Hagan & Schaeff

[57] ABSTRACT

The present invention is directed to a diltiazem formulation suitable for one a day administration. The formulation contains a blend of diltiazem beads having two differing dissolution profiles.

13 Claims, 3 Drawing Sheets

FIG.2

DILTIAZEM FORMULATION

This is a continuation of application Ser. No. 07/872,572, filed Apr. 23, 1992, now abandoned, which in turn is a continuation-in-part of application Ser. No. 07/702,567, filed May 20, 1991 abandoned.

The present invention is directed to diltiazem beads suitable for incorporation into a controlled release diltiazem formulation. Another aspect of this invention is directed to diltiazem formulations suitable for once a day administration.

BACKGROUND OF THE INVENTION

Diltiazem, (+) cis 3-(acetyloxy)-5-[2-(dimethylamino)ethyl]-2,3-dihydro-2-(4-methoxyphenyl)-1,5-benzothiazepin-4(5H)one, is a calcium antagonist that is marketed by Marion Merrell Dow under the tradename Cardizem ®. The compound can be utilized in the treatment of cardiovascular disorders such as angina, arrhythmias, and hypertension. Typical doses range from 120-360 mg/day. Cardizem ® is currently commercially available in two dosage forms in the United States. One of the forms is a rapid release tablet which must be administered from 3-4 times daily. The other is a sustained release tablet which is suitable for bid dosage regimens. A formulation suitable for once a day (qd) administration is not currently commercially available in the United States. Numerous studies have shown that patient compliance increases substantially with medication regimens requiring only one dose per day. Thus it would be a valuable contribution to the art to develop a diltiazem formulation suitable for qd administration.

The pharmacokinetics of a drug can have a considerable impact on whether a particular dosage form will produce satisfactory results after in-vivo administration. Orally administered drugs are absorbed and enter the capillaries and veins of the upper GI tract and are transported by the portal vein directly to the liver before entering the general circulation of the body. The entire absorbed dose of a drug is exposed to the liver during its first pass through the body. If a drug is subject to a high hepatic clearance (i.e. rapidly metabolized by the liver), then a substantial fraction of the absorbed dose is extracted from the blood and metabolized before it reaches the systemic circulation. This phenomenon is termed the first pass effect. The consequence of this phenomenon is a significant decrease in bioavailability. In some instances, the first pass effect is so large as to render oral administration of a drug ineffectual.

The pharmacokinetics of diltiazem have been studied extensively. Diltiazem is well absorbed from the gastrointestinal tract and is subjected to an extensive first pass effect giving an absolute bioavailability of 40% (when compared with intravenous administration.) At therapeutic doses, approximately 60% of the administered diltiazem is metabolized before the compound has had a chance to reach its site of action. Compounds such as diltiazem which are subject to a first pass effect are considered to have non-linear pharmacokinetics. An increase or decrease in the dose administered will not necessarily produce the corresponding increase or decrease in observed blood levels. This is dependent upon whether the metabolic level of the liver has been exceeded.

Authors such as Urquhart et al have recognized that it can be difficult to design extended release formulations for compounds subjected to a first pass effect. CONTROLLED-RELEASE PHARMACEUTICALS, American Pharmaceutical Association (1979). Whereas a rapid release tablet allows saturation of the enzymes and a significant increase in blood levels, a sustained release tablet releasing similar quantities of drugs at a zero order rate will typically not produce such saturation of metabolic capacity. A larger percentage of the sustained release dose will be metabolized before it has had an opportunity to reach its site of action resulting in sub-therapeutic levels over a significant portion of the dosing period.

Controlled release formulations are designed to release significant quantities of drug only at specific timed intervals. If the release occurs at appropriate times, therapeutic levels will be maintained over an extended dosing period such as 12 or 24 hours. An inappropriate release pattern may subject the patient to toxic levels over part of the dosing period and sub-therapeutic levels over other portions of the dosing period. The particular time at which drug should be released varies significantly with each drug and is dependent upon its unique pharmacokinetics. The difficulty of correctly predicting an appropriate release pattern is well known to those skilled in the art.

U.S. Pat. No. 4,894,240 discloses a controlled release diltiazem formulation. The '240 patent states that its formulation is suitable for once a day administration. The formulation is prepared from diltiazem beads in which a diltiazem core is enveloped by a multilayer film in which the film is composed of a major component of a water insoluble polymer and a minor component of a water soluble polymer. Suitable water insoluble polymers include various cellulose esters, polyoxides, polyacrylates, polyethylene, polypropylene, polyurethane, polyvinyl, etc. A proprietary polymer composed of aryrlic resins sold under the tradename, EUDRAGIT, is also specified as being suitable. Suitable water soluble polymers include polyvinylalcohol, polyvinylpyrrolidone, methyl cellulose, and polyethylene glycol. A proprietary acrylate polymer sold under the trademark EUDRAGIT RL is also specified as being suitable. The '240 patent specifies that from 60-95% of the diltiazem should be released from the controlled release dosage form within 13 hours of administration. This release pattern produces peak plasma levels approximately 12-14 hours after administration. Minimal diltiazem is released from the formulation after 13 hours. Although the '240 patent is a valuable contribution to the art, it has been discovered that formulations manufactured with these beads do not maintain optimum blood levels of diltiazem over the entire 24 hour dosing period. Blood levels of diltiazem fall significantly before the next dose is administered resulting in a significant variance between peak and trough levels. Thus it would be a valuable contribution to the art to develop a diltiazem formulation that would optimize diltiazem levels throughout a 24 hour dosing period by minimizing the variance between peak and trough levels.

SUMMARY OF THE INVENTION

A new diltiazem formulation has been discovered that will optimize blood levels of diltiazem over a 24 hour period by decreasing the variance between peak and trough levels of diltiazem. The formulation is a controlled release dosage form which exhibits an in-vitro stair stepped release profile. The stair stepped release profile is characterized by the fact that significant quantities of diltiazem are only released from the formulation at two differing but predetermined time periods. The first in vitro release period is from 1-8 hours after initiation of testing and the second in-vitro release period is approximately 12-21 hours after initiation of testing.

The formulation also exhibits a similar in-vivo release profile. The formulation initially releases significant quantities of diltiazem within the first 8 hours after administration. Minimal diltiazem is released thereafter until approximately 12-16 hours after administration at which point the second release of significant quantities of diltiazem is initiated. The initial release of diltiazem allows the initial obtainment of therapeutic levels of diltiazem and the second release period optimizes diltiazem levels throughout a 24 hour dosing period.

The controlled release profile described above can be obtained by a formulation which contains a blend of diltiazem beads. The blend contains two types of diltiazem beads having differing dissolution rates. One type of bead can be characterized as a rapid release bead. It releases up to 100% of the diltiazem it contains within approximately 6-8 hours of administration. The second bead can be characterized as a delayed release diltiazem bead. Substantial quantities of diltiazem are not released from this bead until approximately 12 hours after administration. The majority of the diltiazem within this bead is released during the time period of 16-24 hours after administration. The diltiazem formulation will typically contain from 25% to 60% w/w of the rapid release beads and more preferably about 40%, and from 40% to 75% w/w of the delayed release bead and more preferably about 60%.

DESCRIPTION OF THE DRAWINGS

FIG. I depicts the typical individual in-vitro dissolution profile of the rapid release beads and the delayed release beads of a preferred formulation encompassed by the instant invention. As is depicted, the majority of the diltiazem contained within the rapid release bead is released within the first 6-8 hours after immersion into the test medium. The release of significant quantities of diltiazem is not typically initiated from the delayed release bead until at least 12 hours after immersion into the test medium.

FIG. II depicts the typical in-vitro dissolution profile of a formulation of the instant invention which contains a blend of the rapid release beads and the delayed release beads. The profile shows that diltiazem is released from the formulation at a significant rate during the first 6-8 hours after initiation of testing. The profile also shows that significant amounts diltiazem are not released from the formulation again until approximately 12-14 hours after initiation of testing. This profile can be characterized as a stair stepped release profile.

DETAILED DESCRIPTION OF THE INVENTION

The rapid release beads of the instant invention will typically exhibit the following vitro dissolution profile when measured in 0.1N HCl:

TABLE I

| HOURS | % DISSOLUTION | % DISSOLUTION PREFERRED |
|---|---|---|
| 3 | 0-40 | 0-20 |
| 6 | 30-100 | ≧50 |

The delayed release beads will exhibit the following in vitro dissolution profile when measured in 0.1N HCl:

TABLE II

| HOURS | % DISSOLUTION | % DISSOLUTION PREFERRED |
|---|---|---|
| 6 | 0-45 | 0-15 |
| 12 | 0-45 | 0-15 |
| 18 | 0-75 | 0-45 |
| 24 | ≧40 | ≧45 |

The diltiazem formulations of the instant invention which contain a blend of rapid release beads and delayed release beads will typically exhibit the following dissolution profile in 0.1N HCl:

TABLE III

| HOURS | % DISSOLUTION | % DISSOLUTION PREFERRED |
|---|---|---|
| 6 | 20-45 | 25-40 |
| 12 | 25-50 | 30-45 |
| 18 | 35-70 | 40-65 |
| 24 | ≧70 | ≧75 |
| 30 | ≧85 | |

Both the rapid release diltiazem beads and the delayed release diltiazem beads are comprised of two parts. The first part is a central core which contains the diltiazem or a pharmaceutically acceptable salt thereof in association with conventional excipients (diltiazem blend). The central core of the rapid release diltiazem beads and the delayed release diltiazem beads may be identical and preferably are.

The second part of the diltiazem beads is a polymeric coating which envelops or substantially envelops the central core. This polymeric coating is responsible for giving the diltiazem bead its particular controlled release characteristics (i.e. for determining whether it is a delayed release or a rapid release bead). The polymeric coating of the rapid release bead and the delayed release bead may be manufactured from different materials. Alternatively, they may be manufactured from the same material, but differing amounts of the polymeric coating are utilized to produce the desired dissolution profile.

As noted above, the central core contains the diltiazem along with conventional excipients. The central core may be prepared by a number of techniques known in the art. Typically the diltiazem blend is bound to an inert carrier with a conventional binding agent. The inert carrier is typically a starch or sugar sphere having a diameter ranging from about 12-45 mesh and more preferably from 35-45 mesh. Sugar spheres are preferred but any pharmaceutically acceptable inert carrier may be utilized.

Before the diltiazem is bound to the inert carrier, it is typically blended with conventional excipients to expedite its handling and to improve the properties of the final dosage form. For example, the diltiazem may be blended with anticaking agents such as talc, microcrystalline cellulose, starch, metallic stearates, or a divalent silicate. It may also be blended with a glidiant such as silicon dioxide, etc., to expedite handling. An acidifying agent is optionally incorporated into the blend as well in order to maintain optimum pH. Examples of suitable acidifying agents include fumaric acid, citric acid, malic acid, adipic acid, ascorbic acid, succinic acid, etc. Other agents that may be blended with the diltiazem include diluents, antimicrobial preservatives, antioxidants, etc.

as is known in the art. The diltiazem blend can be prepared using standard dry mixing techniques as is known in the art.

The quantity of these excipients as well as the amount of diltiazem utilized can vary widely. Typically the blend will have the following composition based upon the total weight of the diltiazem blend (w/w %): (The numerical ranges in Tables IV-VII are being presented in order to further illustrate the invention, but they should not be construed as limiting its scope in any manner).

TABLE IV

| COMPONENT | AMOUNT PRESENT w/w % | PREFERRED AMOUNT w/w % |
|---|---|---|
| DILTIAZEM | 10-90 | 60-70 |
| ANTICAKING AGENT | 10-50 | 15-20 |
| GLIDIANT | 0.1-1 | 0.5 |
| ACIDIFYING AGENT | 0-40 | 15-20 |

The binding agent that is used to secure the diltiazem blend to the inert core is not critical. Any of the known binding agents may be utilized. Typically the binding agent utilized will be a mixture of a lubricating agent and a coating agent. Examples of suitable lubricants include white wax, castor oil, palmitic acid, stearic acid, mineral oil, polyethylene glycol, etc,. Examples of suitable coating agents include ethyl cellulose, methylcellulose, carboxymethylcellulose, hydroxypropymethylcellulose, polyvinylpyrrolidone, polymerized acrylates, etc. Other conventional pharmaceutical excipients may be incorporated into the binding agent as is known in the art. The binding agent is typically produced by admixing the various components into a pharmaceutically acceptable solvent such as isopropyl alcohol until a uniform mixture is obtained.

The quantity of lubricating agent, coating agent, as well as the solvent that is utilized in the preparation of the binding agent, can vary widely. Typically the binding agent will have the following composition based upon the total weight of the binding agent w/w %:

TABLE V

| COMPONENT | AMOUNT PRESENT w/w % | PREFERRED AMOUNT w/w % |
|---|---|---|
| LUBRICANT | 0-15 | 0.25-5 |
| COATING AGENT | 1-30 | 1-15 |
| SOLVENT | 55-99 | 80-95 |

The quantity of diltiazem blend and binding agent utilized in preparing the central core can vary widely. Typically the central core will have the following composition based upon the total weight of the central core after proper drying (w/w %):

TABLE VI

| COMPONENT | AMOUNT PRESENT w/w % | PREFERRED AMOUNT w/w % |
|---|---|---|
| DILTIAZEM BLEND | 50-95 | 80-90 |
| BINDING AGENT | 1-10 | 3-7 |
| INERT CORE | 3-30 | 10-15 |

The central core is then produced by utilizing the binding agent to attach the powdered diltiazem blend to the solid carrier. This can be accomplished by means known in the art for producing pharmaceutical beads. Suitable means include utilization of a conventional coating pan, an automatic coating machine, or a rotogranulator.

Alternatively, the central core may be prepared by admixing the diltiazem blend with a diluent/binder such as microcrystalline cellulose and the binding agent described above. This blend is wet granulated until diltiazem granules are formed. These granules are then dried and may be coated with a polymeric coating in the same manner as the central cores described above. The amount of microcrystaline cellulose used can vary widely but will range from 5-50w/w % in the dried granule. The diltiazem blend and binding agent will be present in conventional amounts typically utilized in the production of granules. The central core may also be prepared by compression or by extrusion spheronization of the diltiazem blend as is known in the art.

The second component of the diltiazem beads is the polymeric coating. As noted above, the polymeric coating is responsible for giving the diltiazem bead its particular release characteristics (i.e. for determining whether it is a rapid release or a delayed release bead). The composition of the polymeric material as well as the amount of material that is utilized will affect whether the particular diltiazem bead gives the desired dissolution characteristics.

The composition of the polymeric coating utilized for producing the delayed release bead as well as the amount of this polymeric coating is the key to obtaining the dissolution rate described above. The polymeric coating may be produced from polymerized acrylates or copolymers of acrylic acid and methacrylic acid or esters of either monomer (hereinafter polymerized acrylates). The polymeric coating of the delayed release pellet may also be prepared from one of the organosiloxane oral coating materials known in the art such as polydimethylsiloxane, polydiethylsiloxane, etc.

Polymerized acrylates as well as copolymers of acrylic acid and methacrylic acid or esters of either monomer are known in the art and are available from many commercial sources. Examples of such copolymers include poly(methyl methacrylate), poly(ethyl methacrylate), poly(butyl methacrylate), poly(isobutyl methacrylate), poly(isobutyl methacrylate), poly(phenyl methacrylate) etc. The amount of polymerized acrylates contained within the polymeric coating can vary. Typically the polymeric coating will contain from 10 to 75 w/w % of polymerized acrylate and more preferably about 55-65 w/w % based upon the total weight of the polymeric coating of a dried diltiazem bead. Similar quantities of the organosiloxane oral coating material may be used.

Preferred polymerized acrylates are those which are water insoluble/slightly water permeable copolymers of acrylic acid lower alkyl ester and methacrylic acid lower alkyl ester in which some ester moieties are further substituted with a tri(alkyl) ammonium group. The tri(alkyl) ammonium group is typically present in the range of about 1:30 to 1:50 relative to the amount of neutral ester present. One such preferred copolmer is a copolymer of ethyl acrylate and methyl methacrylate which contains trimethylammoniumethyl methacrylate in a range of about 1:40 relative to the neutral monomers. This copolymer is commercially available from Rohm Pharma Gmbh under the tradename Eudragit RS.

It is also preferred to incorporate into the polymeric coating a minor amount of a water insoluble/freely water permeable copolymer of acrylic acid lower alkyl ester and methacrylic acid lower alkyl ester in which some ester moieties are further substituted with a tri(alkyl) ammonium group. The tri(alkyl) ammonium group is present in the range of about 1:20 relative to the amount of methacrylic and acrylic monomer utilized. One such preferred copolymer is a copolymer of ethyl acrylate and methyl methacrylate which contains trimethylammoniumethyl methacrylate in a range of about 1:20 relative to the neutral monomers. This copolymer is also commercially available from Rohm Pharma Gmbh under the tradename Eudragit RL. The utilization of this water insoluble/freely water permeable methacrylic copolymer is optional. If utilized, the ratio of water insoluble/slightly permeable acrylate to water insoluble/freely permeable acrylate will be 100:0 to 70:30 and more preferably about 95:5.

The polymeric coating may optionally contain a sufficient quantity of a suitable plasticizer. Examples of such plasticizers include acetyl triethyl citrate, dibutyl phthalate, tributyl citrate, triethyl citrate, acetyl tributyl citrate, propylene glycol, triacetin, polyethylene glycol and diethyl phthalate. Preferred plasticizers are tributyl citrate and acetyl tributyl citrate. The amount plasticizer utilized can vary, but will typically be present in the amount of 0 to 40 w/w % based upon the total weight of the polymeric coating of a dried diltiazem bead, and more preferably about 5–15 w/w %.

In addition to containing polymerized acrylate and optionally a plasticizer, the polymeric coating may contain conventional excipients including antifoaming agents such as simethicone, in the range of 0–2 w/w % based upon the total weight of the polymeric coating of a dried diltiazem bead. It may also contain an antiadherant such as talc in the range of from 0–70w/w % and more preferably about 25–35 w/w % based upon the total weight of the polymeric coating of a dried diltiazem bead. The polymeric coating may also contain other pharmaceutical excipients as is known in the art.

A sufficient quantity of the polymeric coating must be utilized to substantially envelop the central core in order to give it the desired delayed release characteristics. The exact quantity polymeric coating can vary depending upon the composition of the central core and the manner in which it is produced. For example, factors that may affect the amount of polymeric coating required include the size of the central core, the size of any inert carrier used in producing the central core, whether the central core was produced via compression or granulation, the composition of the binding agent, and the amount of binding agent utilized. The exact amount required can be calculated by one skilled in the art utilizing the dissolution profile taught above for the delayed release bead. Typically though based upon the total weight of the delayed release diltiazem beads, after proper drying, the polymeric coating will be present in the quantity of from about 15–50 w/w % and more preferably from 25–30 w/w % and most preferably about 25 w/w %. The central core will contribute the rest of the beads weight (i.e. from 50–80 w/w).

The polymeric coating of the rapid release pellet may be made from a variety of coating materials that are typically utilized in the pharmaceutical arts. The coating may be manufactured from a variety of water insoluble polymers such as, for example, ethylcellulose, cellulose acetate, cellulose propionate, cellulose acetate butyrate, polyethylene, polypropylene, polyethylene oxide, polyvinyl acetate, polyvinyl chloride, etc. A minor proportion of a water soluble polymer may also be included in the polymeric coating. Examples of such polymers include methyl cellulose, hydroxypropyl cellulose, polyethylene glycol, polyvinyl pyrrolidone, etc. These coatings may also include conventional excipients such as plasticizers, antifoaming agents, antiadherants, etc. The quantity of polymeric coating that is required to give the desired release characteristics of the rapid release pellet can vary widely and will depend upon the particular polymer or mixture thereof chosen. This amount can readily be determined by one skilled in the art utilizing the dissolution profile taught in this specification above.

The polymeric coating of the rapid release pellet may also be prepared from a polymerized acrylate or organosiloxane as described above for the delayed release pellet. It is preferred that the polymeric coating of the rapid release pellet also be prepared from a copolymer of ethyl acrylate and methyl methacrylate which contains trimethylammoniumethyl methacrylate in a range of about 1:40 relative to the neutral monomers. It is also preferable to incorporate a minor amount of a copolymer of ethyl acrylate and methyl methacrylate which contains trimethylammoniumethyl methacrylate in a range of about 1:20 relative to the neutral monomers. This coating also preferably includes one of the plasticizers described above for the delayed release pellet as well as an anti-adherant and anti-foaming agent. The particular quantity of polymerized acrylate, plasticizer anti-adherant, and anti-foaming agent that is utilized to prepare the polymeric coating material will fall within the ranges described above for the delayed release bead. The amount of this polymeric coating that is applied to the rapid release pellet will be a quantity such that, after proper drying, the polymeric coating will contribute from 10–15 w/w % of the total weight of the diltiazem bead and preferably about 12–13 w/w %. The central core will contribute the other 85–90 w/w % of the diltiazem bead.

The polymeric coating of the either the rapid release or delayed release bead may be applied to the central core using methods and techniques known in the art. Typically a suspension, emulsion, or solution of the polymeric coating is prepared as is known in the art. The amount of fluidized polymeric coating required in the coating proces may be readily calculated depending upon the amount of polymeric coating desired in the dried diltiazem beads. The fluid polymeric coating may be applied to the central core by a number of coating techniques known in the art. Examples of suitable coating devices include fluid bed coaters, pan coaters, etc. After the polymeric coating has been applied to the central core, the diltiazem beads are then dried until the beads have the desired dissolution profile described above. After drying, the proper ratio of rapid release beads and delayed release beads are blended together for incorporation into a final dosage form. The particular ratio of rapid release beads to delayed release beads can vary but will typically fit within the guidelines disclosed above.

The blended diltiazem beads may be administered by a number of dosage forms known in the art. For example, they may be placed into soft or hard gelatin capsules. The blended beads may be admixed with a binder such as microystalline cellulose and compressed into tablets. Alternatively, they may be placed in a liquid immediately prior to administration and administered as a suspension. Methods for producing these various dosage forms are known to those skilled in the art.

The quantity of diltiazem beads that are placed in each dosage form can vary widely. However, typically a quantity of beads will be utilized to produce a final dosage form containing from 90 mg-540 mg of diltiazem and more preferably from 120 mg-360 mg. The final dosage form containing the rapid release and delayed release beads is suitable for once a day administration. It may be used for a variety of cardiovascular indications such as angina, hypertension, arrhythmias, etc., as is known in the art. The diltiazem formulations of the instant invention may contain other antihypertensive, antiarrhythmic, or antianginal medications that are known in the art. Examples of such medications include diuretics such as hydrochlorothizes, furosemide, etc., ACE inhibitors such as captopril, enalpril, etc, B-blockers such as propranolol, etc.

As used in this application:

a) any reference in the specification or claims to an in-vitro dissolution profile should be construed as referring to a dissolution test in which the total amount of diltiazem released is measured as in the US Pharmacopeia, Volume XXII, utilizing a Type 2 paddle assembly at 100 rpm, a temperature of 37° C. and a test solution of 0.1N HCl and utilizing a quantity of diltiazem beads sufficient to accurately measure.

b) the terms diltiazem beads and diltiazem pellets are used interchangeably and refer to a diltiazem containing central core which is substantially enveloped by a release controlling material and;

c) the terms polymeric coating and polymeric coating material are used interchangeably and refer to the release controlling material that surrounds the central core.

The following example is presented in order to further illustrate the invention, but it should not be construed as limiting the invention in any manner.

EXAMPLE I

The following example presents one formulation encompassed by the present invention. Table VII presents the composition of the dosage forms prepared in Examples I and II.

TABLE VII

| Item | mg/capsule |
|---|---|
| Diltiazem HCl | 180.0* |
| Fumaric Acid, NF | 45.00 |
| Talc, USP | 45.00 |
| Silicon Dioxide, NF | 1.355 |
| Sugar Spheres | 38.75 |
| White Wax, NF** | 4.310 |
| Ethylcellulose, NF** | 8.598 |
| Castor Oil, USP** | 2.840 |
| Stearic Acid, NF** | 1.420 |
| Eudragit RS 30 D Solids | 55.13 |
| Eudragit RL 30 D Solids | 2.823 |
| Acetyl Tributyl Citrate | 11.39 |
| Talc, USP | 28.23 |
| Simethicone Emulsion, USP | 0.100 |
| Total | 424.5 |

METHOD OF MANUFACTURE

I. PREPARATION OF CENTRAL CORE

A) PREPARATION OF DILTIAZEM BLEND

To an 80 cubic foot blender is charged 188 kg of diltiazem HCl, 94.0 kg of fumaric acid NF, 94 kg of talc, 2.8 kg of silicon dioxide, and an additional 188 kg of diltiazem HCl. The mixture is dry blended for 15 minutes and then milled through a 0.013 inch screen.

B) PREPARATION OF BINDING AGENT

To a 300 gallon tank is added 652 kg of isopropyl alcohol (99%). The alcohol is continuously agitated and warmed to a temperature of 55° C. 24.2 Kg of ethylcellulose, 8 kg of castor oil, 4 kg of stearic acid, and 12.2 kg of melted white wax are added to the alcohol while maintaining agitation. The mixture is then cooled to 25° C.

C) ATTACHMENT OF DILTIAZEM BLEND TO SOLID CARRIER

The diltiazem blend is bound to the inert carrier using the following sequential coating technique (thereby producing the central core). A coating pan is loaded with 80 kg of the diltiazem blend produced immediately above, 72.6 kg of the binding agent produced immediately above, and 80 kg of 35-45 mesh sugar spheres. Coating is initiated and continued until the supply of binding agent is exhausted. The resulting central cores (stage 1) are then dried in the coating pan and screened as required. 82 Kg of these stage 1 central cores are placed in a coating pan along with an additional 80 kg of diltiazem blend and 72.6 kg of binding agent. Coating is initiated and continued until the supply of binding agent is exhausted. The resulting central cores (stage 2) are dried in the coating pan and screened as required. 82 kg of these stage 2 central cores are placed in a coating pan along with an additional 80 kg of diltiazem blend and 72.6 kg of binding agent. Coating is initiated and continued until the supply of binding agent is exhausted. The resulting central cores (stage 3) are dried in the pan and screened as required.

II. PREPARATION OF POLYMERIC COATING

A stainless steel tank is charged with 371 kg of purified water, 40 kg of talc, and mixed to produce a talc suspension. A second steel tank is charged with 259.5 kg of Eudragit RS 30D (acrylate polymer) and 0.14 kg of simethicone emulsion USP. The mixture is slowly agitated. While maintaining agitation, 13.3 kg of Eudragit RL 30D (acrylate polymer) and 16.1 kg of acetyltributyl citrate are added to the second tank. The talc suspension produced above is then added to the second tank and stirred for 60 minutes.

III. PREPARATION OF RAPID RELEASE BEAD

A Wurster coater is charged with 175 kg of the stage 3 central cores produced above and 144.45 kg of the polymeric coating produced above. The coating process is continued until the supply of polymeric coating is exhausted. The resulting diltiazem beads are then dusted with 4.2 kg of talc and dried in an oven at 50° C. for at least 144 hours or until the beads exhibit the following dissolution profile in 0.1N HCl when measured by the methods of the U.S. Pharmacopeia XXII with a type 2 paddle assembly at 100 rpm:

| HOURS | % DISSOLUTION |
|---|---|
| 3 | 0-15 |
| 6 | 60-90 |

IV. PREPARATION OF DELAYED RELEASE BEAD

A Wurster coater is charged with 145 kg of the stage 3 central cores produced above and 285.95 kg of the polymeric coating produced above. The coating process is continued until the supply of polymeric coating is exhausted. The resulting diltiazem beads are then dusted with 4.2 kg of talc and dried in an oven at 50° C.

for at least 168 hours or until the beads exhibit the following dissolution profile in 0.1N HCl when measured by the method of the U.S. Pharmacopeia XXI using a type 2 paddle assembly at 100 rpm:

| HOURS | % DISSOLUTION |
|-------|---------------|
| 6     | 0-5           |
| 12    | 0-10          |
| 18    | 0-35          |
| 24    | 50-90         |

V. PREPARATION OF DILTIAZEM DOSAGE FORM 208.2 Kg of rapid release diltiazem beads and 363 kg of delayed release diltiazem beads are placed in a blender and mixed for 15 minutes. The diltiazem beads are then encapsulated utilizing a capsule filling machine to produce a final dosage form containing 180 mg of diltiazem.

VI. IN-VITRO DISSOLUTION CHARACTERISTICS

The in vitro dissolution profile of the rapid release beads, delayed release beads and the diltiazem capsules containing the blended diltiazem beads is determined by the method of the U.S. Pharmacopeia XXII, using a type 2 paddle assembly at 100 rpm, 37° C., in 0.1N HCl. The amount of diltiazem released was measured with a HP - Diode Ray.

| Time | Blended Formulation | Rapid Release Beads | Delayed Release Beads |
|------|---------------------|---------------------|-----------------------|
| 3    | 2.0                 | 3.1                 | 1.2                   |
| 6    | 25.7                | 79.4                | 1.4                   |
| 9    | 29.2                | 92.2                | 1.5                   |
| 12   | 30.3                | 94.5                | 2.0                   |
| 15   | 32.3                | 95.8                | 4.2                   |
| 18   | 44.9                | 96.8                | 21.7                  |
| 21   | 68.3                | 97.6                | 55.7                  |
| 24   | 82.9                | 98.4                | 76.2                  |
| 30   | 91.3                | 99.7                | 87.0                  |

EXAMPLE II

This example demonstrates the preparation of a formulation of the instant invention. The final dosage form has the same composition as in Table VII above.

I. Preparation of Central Core

A) PREPARATION OF DILTIAZEM BLEND

To an 80 cubic foot blender is charged 188.0 kg of diltiazem HCl, 94.0 kg of fumaric acid NF, 94.0 kg of talc, 2.8 kg of silicon dioxide, and an additional 188.0 kg of diltiazem HCl. The mixture is dry blended for 15 minutes and then milled through a 0.013 inch screen using a conventional milling machine to a sufficiently fine particle size, averaging about 75 microns.

B) PREPARATION OF BINDING AGENT

To a 300 gallon tank is added 652.0 kg of isopropyl alcohol (99%). The alcohol is continuously agitated and warmed to a temperature of 55° C. 24.2 kg of ethylcellulose, 8.0 kg of castor oil, 4.0 kg of stearic acid, and 12.2 kg of melted white wax are added to the alcohol while maintaining agitation. The mixture is then cooled to 25° C.

C) ATTACHMENT OF DILTIAZEM BLEND TO SOLID CARRIER

The diltiazem blend is bound to the inert carrier using the following sequential coating technique (thereby producing the central core). A coating pan is loaded with 80.0 kg of 35-45 mesh sugar spheres and rotation is begun. The sugar spheres are sprayed with the binding agent, produced immediately above, until they became sufficiently adhesive to allow the application of the diltiazem blend produced immediately above. 80.0 kg of the diltiazem blend is applied simultaneously with approximately 73 kg of the binding agent. The bead bed temperature was maintained in the range of 16° to 20° C., preferably 17°-18° C., during the application of the powder blend and binding agent. Coating is continued until the supply of diltiazem blend is exhausted. The resulting central cores (Stage 1) are then dried in the coating pan and screened through appropriate size screens to remove oversize and undersize material. 82.0 kg of these stage 1 central cores are placed in a coating pan and rotation is begun. The stage 1 central cores are sprayed with the binding agent, produced immediately above, until they became sufficiently adhesive to allow the application of additional diltiazem blend produced immediately above. An additional 80.0 kg of the diltiazem blend is applied simultaneously with approximately 73 kg of the binding agent. The bead bed temperature is maintained in the range of 16° to 20° C., preferably 17°-18° C., during the application of the powder blend and binding agent. Coating is continued until the supply of diltiazem blend is exhausted. The resulting central cores (Stage 2) are then dried in the coating pan and screened through appropriate size screens to remove oversize and undersize material. 82.0 kg of these stage 2 central cores are placed in a coating pan and rotation is begun. The stage 2 central cores are sprayed with the binding agent, produced immediately above, until they become sufficiently adhesive to allow the application of additional diltiazem blend produced immediately above. An additional 80.0 kg of the diltiazem blend is applied simultaneously with approximately 73 kg of the binding agent. The bead bed temperature is maintained in the range of 16° to 20° C., preferably 17°-18° C., during the application of the powder blend and binding agent. Coating is continued until the supply of diltiazem blend is exhausted. The resulting central cores (Stage 3) are then dried in the coating pan and screened through appropriate size screens to remove oversize and undersize material.

II. Preparation of Polymeric Coating

A stainless steel tank is charged with 371.0 kg of purified water, 40.0 kg of talc, and mixed to produce a talc suspension. A second steel tank is charged with 259.5 kg of Eudragit RS 30 D (acrylate polymer) and 0.14 kg of simethicone emulsion USP. The mixture is slowly agitated. While maintaining agitation, 13.3 kg of Eudragit RL 30 D (acrylate polymer) and 16.1 kg of acetyltributyl citrate are added to the second tank. The talc suspension produced above is then added to the second tank and stirred for 60 minutes.

III. Preparation of Rapid Release Bead

A Wurster coater is charged with 175 kg of the stage 3 central cores produced above and the cores are coated with approximately 145 kg of the polymeric coating produced above. The coating process is continued until the supply of polymeric coating is exhausted. The diltiazem beads are coated while maintaining a product temperature in the range of 20°-35° C., preferably 26°-30° C. The resulting diltiazem beads are dusted with 4.25 kg of talc and dried in an oven at 50° C. for 144 hours or until the beads exhibit the following dissolution profile in 0.1N HCl when measured by the U.S. Pharmacopeia XXII using a type 2 paddle assembly at 100 RPM:

| HOURS | % DISSOLUTION |
|---|---|
| 3 | 0–15 |
| 6 | 60–90 |

IV. Preparation of Delayed Release Bead

A Wurster coated is charged with 145 kg of the stage 3 central cores produced above and the cores are coated with approximately 286 kg of the polymeric coating produced above. The coating process is continued until the supply of polymeric coating is exhausted. The diltiazem beads are coated while maintaining a product temperature in the range of 20°–35° C., preferably 26°–30° C. The resulting diltiazem beads are then dusted with 4.2 kg of talc and dried in an oven at 50° C. for 168 hours or until the beads exhibit the following dissolution profile in 0.1N HCl when measured by the U.S. Pharmacopeia XXII in a type 2 paddle assembly at 100 RPM:

| HOURS | % DISSOLUTION |
|---|---|
| 6 | 0–5 |
| 12 | 0–10 |
| 18 | 0–35 |
| 24 | 50–90 |

V. Preparation of Diltiazem Dosage Form 202.8 kg of rapid release diltiazem beads and 363.4 kg of delayed release diltiazem beads are placed in a blender and mixed for 15 minutes. The diltiazem beads are then encapsulated utilizing a capsule filling machine to produce a final dosage form containing an amount of beads such that the capsules contained 180 mg of diltiazem. The weight of fill was determined based on the drug potency of the bead blend.

VI. In-vitro Dissolution Characteristics

The in vitro dissolution profile of the rapid release beads, delayed release beads and the diltiazem capsules containing the blended diltiazem beads is determined by the method of the U.S. Pharmacopeia XXII, using a type 2 paddle assembly at 100 rpm, 37° C., in 0.1N HCl. The amount of diltiazem released was measured with a HP - Diode Ray.

| TIME | RAPID RELEASE BEADS | DELAYED RELEASE BEADS | BLENDED FORMULATION |
|---|---|---|---|
| 3 Hr | 1.3 | 0.0 | 0.3 |
| 6 Hr | 70.1 | 0.9 | 23.8 |
| 9 Hr | 93.1 | 2.4 | 32.6 |
| 12 Hr | 96.6 | 3.9 | 34.6 |
| 15 Hr | 98.2 | 6.0 | 36.8 |
| 18 Hr | 99.4 | 17.4 | 43.8 |
| 21 Hr | 100.4 | 52.5 | 66.9 |
| 24 Hr | 101.1 | 79.6 | 87.0 |
| 30 Hr | 102.1 | 92.1 | |

EXAMPLE 3—PHARMACOKINETIC STUDY

I. Preparation of Diltiazem Dosage Form

Rapid Release Beads and Delayed Release Beads were blended and filled into capsules which had been prepared in a manner similar to those of example 2. The capsules were filled with an amount of beads such that the filled capsules would contain 120 mg of the diltiazem. The weight of fill was determined based on the drug potency of the bead blend.

The in vitro dissolution profile of the diltiazem capsules containing the blended diltiazem beads was determined by the method of the U.S. Pharmacopeia XXII, using a type 2 paddle assembly at 100 rpm, 37 C., in 0.1N HCL. The amount of diltiazem released was measured with a HP - Diode Ray. The percent of diltiazem release over time is listed below in Table 1.

TABLE VIII

| TIME | 120 mg Capsules of Blended Formulation |
|---|---|
| 3 Hr | 7.4% |
| 6 Hr | 36.2% |
| 9 Hr | 43.2% |
| 12 Hr | 45.4% |
| 15 Hr | 48.1% |
| 18 Hr | 58.4% |
| 24 Hr | 92.4% |

II. Pharmacokinetic Bioavailability Study

A study was conducted with the diltiazem capsules described above to determine the relative bioavailability of the diltiazem from the once a day capsule formulations, when tested in human subjects. The study consisted of twenty-four healthy male volunteers between the ages of 19 and 45 years, who participated in the randomized, four-way, crossover study design. The diltiazem was administered as 120 mg capsules for 7 doses of the sustained release formulation and an oral solution (120 mg) was used as reference given as 40 mg doses three times a day for 21 doses.

Blood (plasma) samples were collected just prior to the 1st dose. Additional samples were obtained following the multiple oral doses as follows:

For the 40 mg oral solution reference—just prior to the 16th dose, just prior to the 19th dose and 0, 0.5, 1, 1.5. 2, 4, 6, and 8 hours following the 19th dose and 0.5, 1, 1.5, 2, 4, 6, and 8 hours after the 20th dose and 0.5, 1.0, 1.5, 2.0, 4.0, 6.0, 8.0, 10.0, 12.0, and 14.0 hours following the 21st dose. For the sustained release capsule formulations—just prior to the 6th dose, just prior to the 7th dose and 2, 4, 6, 8, 10, 12, 14, 16, 18, 20, 22, 24, 26, 28, and 30 hours after the 7th dose.

Figure 1:
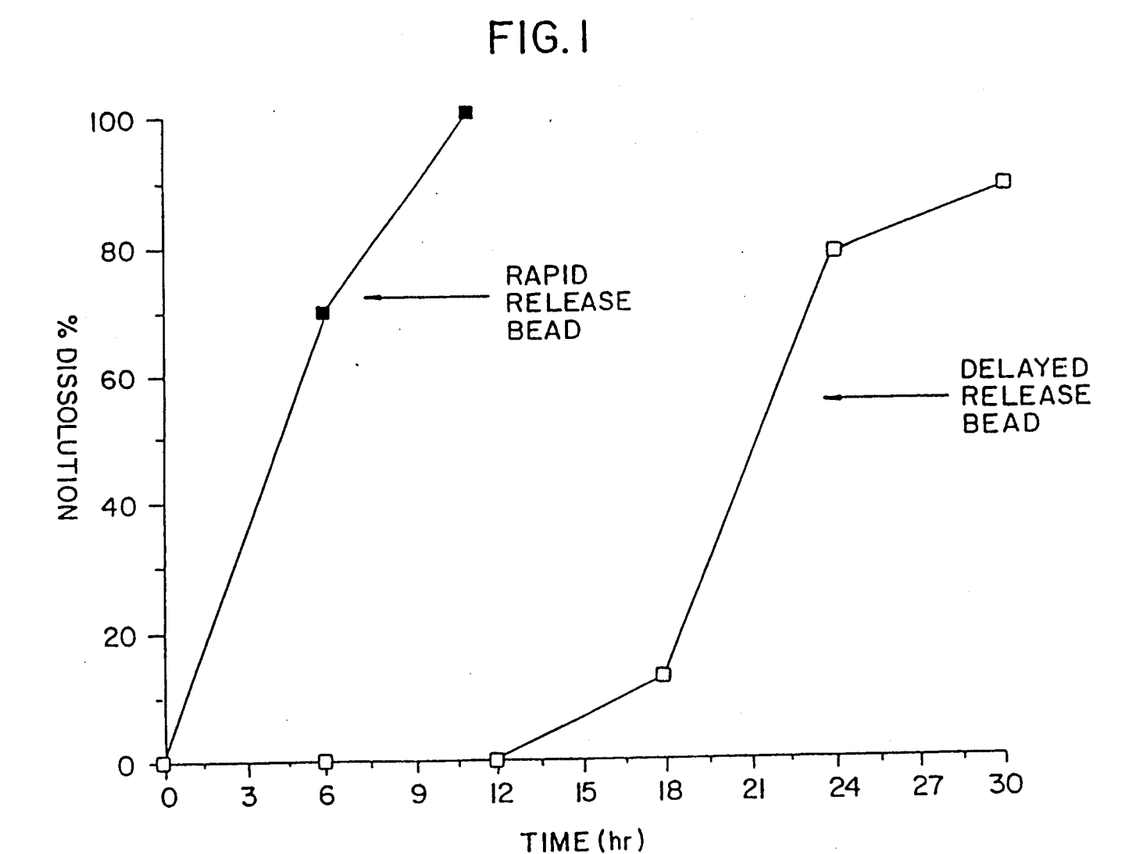
Figure 2:
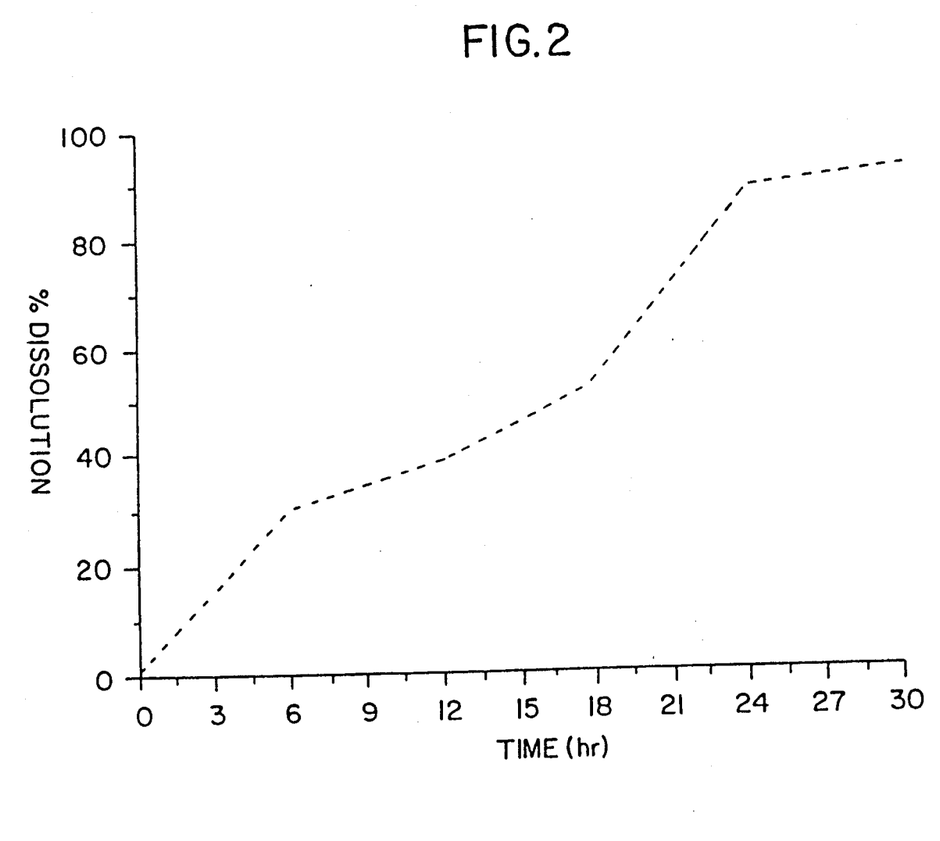

Plasma concentrations of the diltiazem and metabolites were determined by HPLC analysis. Model-independent pharmacokinetic data analysis was performed on the resultant plasma diltiazem concentration—time data. The plasma concentration time data for the oral solution following the 19th, 20th and 21st dose is listed in Table 2, and the plasma time concentration data for the once a day capsule formulation described above after the 6th dose is listed in Table 3. The data listed is a mean of 22 subjects. FIG. 1 is a plot of the diltiazem plasma concentration—time profile for the oral solution and the once a day capsule formulation described above for the 24 hours on day 7 of treatment.

TABLE IX

| Time | Mean Plasma Concentration Oral Solution (ng.mL) |
|---|---|
| 19th Dose: | |
| 0 hours | 20.1 |
| 0.5 hours | 50.1 |
| 1 hour | 71.3 |
| 1.5 hours | 71.7 |
| 2 hours | 67.1 |
| 4 hours | 42.7 |
| 6 hours | 36.1 |
| 8 hours | 19.3 |
| 20th Dose: | |
| 0.5 hours | 27.1 |
| 1 hour | 44.6 |
| 1.5 hours | 49.5 |
| 2 hours | 52.0 |
| 4 hours | 41.7 |
| 6 hours | 26.6 |
| 8 hours | 19.1 |
| 21st Dose: | |
| 0.5 hours | 29.2 |
| 1 hour | 49.3 |
| 1.5 hours | 50.6 |
| 2 hours | 50.6 |
| 4 hours | 35.5 |
| 6 hours | 26.5 |
| 8 hours | 19.6 |
| 10 hours | 16.5 |
| 12 hours | 12.6 |
| 14 hours | 9.4 |

TABLE X

| Time | Mean Plasma Concentration Once a Day Formulation (ng/mL) (Invention) |
|---|---|
| 7th Dose: | |
| 0 hours | 26.6 |
| 2 hours | 24.9 |
| 4 hours | 29.6 |
| 6 hours | 56.8 |
| 8 hours | 50.2 |
| 10 hours | 43.4 |
| 12 hours | 39.1 |
| 14 hours | 40.4 |
| 16 hours | 39.1 |
| 18 hours | 33.4 |
| 20 hours | 27.5 |
| 22 hours | 24.2 |
| 24 hours | 22.4 |
| 26 hours | 20.1 |
| 28 hours | 17.7 |
| 30 hours | 15.2 |

The Mean values for the following pharmacokinetic parameters were determined from the plasma concentration time profiles: AUC—Area under the curve, Cmax—Maximum plasma concentration, Trough—minimum plasma concentration, Ratio—ratio of C-max to C-min, Tmax—time to maximum concentration, and F—relative bioavailability as compared to the oral solution reference. The mean values for the oral solution and the once a day diltiazem capsules described above are listed in Table XI.

TABLE XI

| Pharmacokinetic Parameter | Oral Solution | Once a Day Capsule |
|---|---|---|
| AUC | 910.3 ng/mL × hr | 849.1 ng/mL × hr |
| Cmax | 78.6 ng/mL | 54.4 ng/mL |
| Trough | 19.8 ng/mL | 24.7 ng/mL |
| Ratio | 4.7 | 2.9 |
| Tmax | 1.3 hours | 7.3 |
| F | 1.0 | 0.93 |

The formulation of the instant invention containing a blend of Rapid Release Beads and Delayed Release Beads, which was described above, was considered to be a once a day formulation based on the acceptable relative bioavailability, acceptable minimum concentration and acceptable ratio of maximum to minimum concentration. The relative bioavailability of this formulation given once a day was 93.3% when compared to the 40 mg solution given three times a day. The mean steady-state trough values were 24.7 ng/mL for the qd formulation compared to 19.8 ng/mL for the reference solution. The mean Cmax/Cmin ratio for the qd formulation was 2.9 compared to 4.7 for the reference treatment, indicating good sustained release profile. Mean maximum plasma concentration for the once a day patent formulation was 54.5 ng/mL compared to 78.6 ng/mL for the reference solution.

Figure 3:
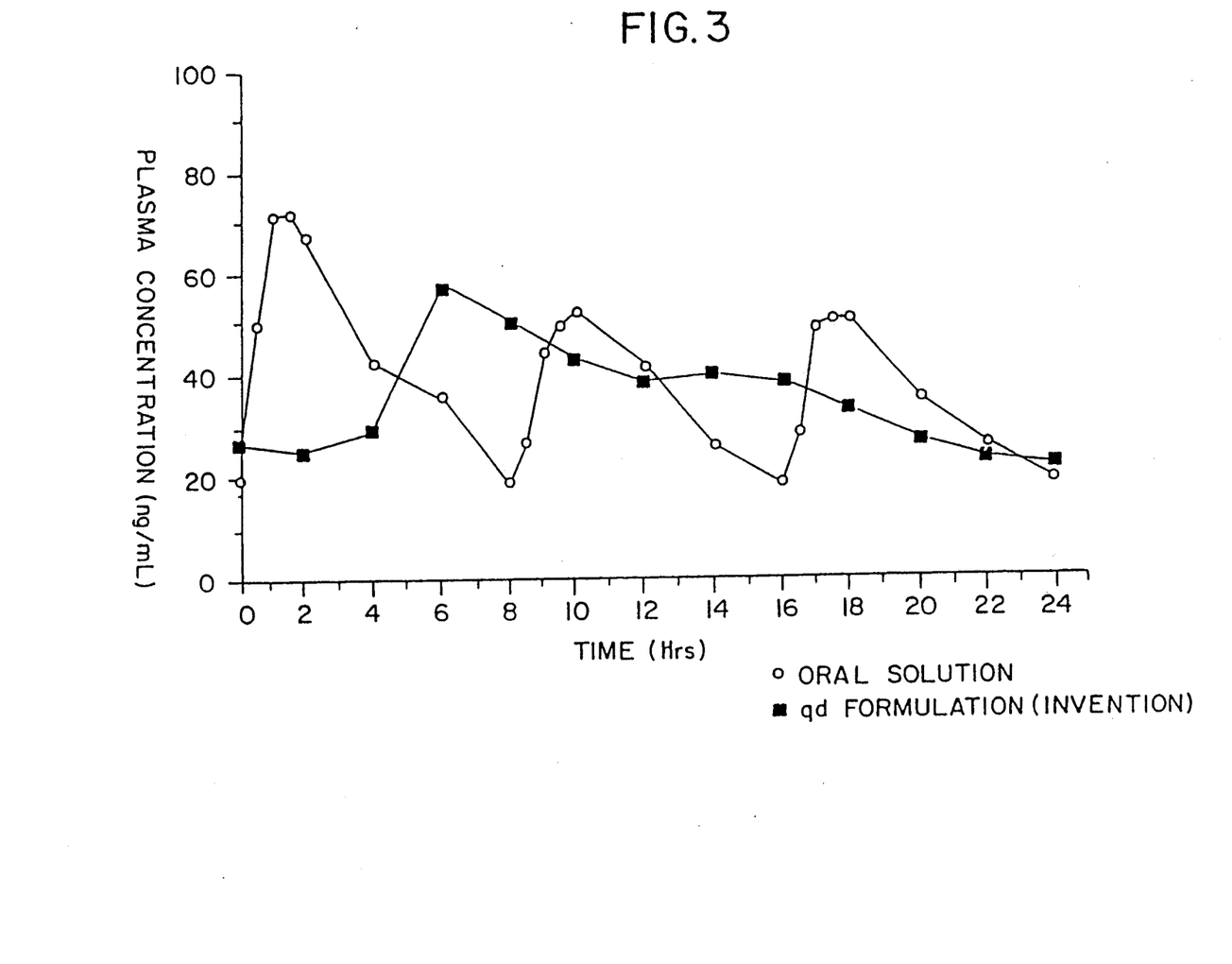

Note in the table above that the trough value is the mean trough level for day 6, 7 and 8 of the study. The ratio (Cmax/Cmin) is determine within individual subjects and the F is based on matched subjects in the design. FIG. 3 graphically depicts the data contained in Table IX and X.

What is claimed is:

1. A diltiazem formulation suitable for once-a-day oral administration comprising a blend of:
   A) a sufficient quantity of rapid release diltiazem beads which further comprise
      1) a diltiazem core containing an effective amount of diltiazem of a pharmaceutically acceptable salt thereof, optionally in association with pharmaceutically acceptable excipients and;
      2) a sufficient quantity of a first suitable polymeric coating material which substantially envelops said diltiazem core so that said diltiazem bead exhibits the following in-vitro dissolution profile when measured in a type 2 dissolution apparatus (paddle) according to U.S. Pharmacopeia XXII at 37° C. at 100 rpm:
         a) from 0–40% of total diltiazem is released after 3 hours of measurement in said apparatus, and;
         b) from 30–100% of total diltiazem is released after 6 hours of measurement in said apparatus, and;
   B) a sufficient quantity of delayed release diltiazem beads which further comprise:
      1) a central core containing an effective amount of diltiazem or a pharmaceutically acceptable salt thereof, optionally in association with pharmaceutically acceptable excipients, and;
      2) a sufficient quantity of a second suitable polymeric coating material which substantially envelops said diltiazem core so that said diltiazem bead exhibits the following in-vitro dissolution profile when measured in a type 2 dissolution apparatus (paddle) according to U.S. Pharmacopeia XXII, at 37° C. in 0.1N HCl at 100 rpm:
         a) from 0–15% of total diltiazem is released after 12 hours in said apparatus;
         b) from 0–45% of total diltiazem is released after 18 hours of measurement in said apparatus, and;

c) not less than 45% of total diltiazem is released after 24 hours of measurement in said apparatus, wherein said blend exhibits the following in-vitro dissolution pattern when measured in a type 2 dissolution apparatus (paddle), according to U.S. Pharmacopeia XXII, in 0.1N HCl at 100 rpm:
  a) from 20-45% of total diltiazem is released after 6 hours of measurement in said apparatus;
  b) from 25-50% of total diltiazem is released after 12 hours of measurement in said apparatus;
  c) from 35-70% of total diltiazem is released after 18 hours of measurement in said apparatus;
  d) not less than 70% of total diltiazem is released after 24 hours of measurement in said apparatus; and
  e) not less than 85% of total diltiazem is released after 30 hours of measurement in said apparatus.

2. A diltiazem formulation according to claim 1 in which said second polymeric coating of said delayed release diltiazem bead contains from 10-75 w/w % of polymerized acrylate based upon the total weight of the polymeric coating of a dried delayed release diltiazem bead.

3. A diltiazem formulation according to claim 2 in which said second polymeric coating comprises from 15-50 w/w % of the total weight of a dried delayed release diltiazem bead.

4. A diltiazem formulation according to claim 3 in which said polymerized acrylate is a copolymer of ethyl acrylate and methyl methacrylate which contains trimethylammoniumethyl methacrylate in a range of about 1:40 relative to the neutral monomers.

5. A diltiazem formulation according to claim 4 in which said second polymeric coating contains a plasticizer in the range of 5-15 w/w % based upon the total weight of the polymeric coating of a dried delayed release diltiazem bead.

6. A diltiazem formulation according to claim 5 in which said plasticizer is tributyl citrate and acetyl tributyl citrate.

7. A diltiazem formulation according to claim 6 in which said second polymeric coating comprises about 25 w/w % of the total weight of a dried delayed released diltiazem bead.

8. A diltiazem formulation according to claim 7 in which said second polymeric coating contains
  a) a copolymer of ethyl acrylate and methyl methacrylate which contains trimethylammoniumethyl methacrylate in a range of about 1:40 relative to the neutral monomers and
  b) a copolymer of ethyl acrylate and methyl methacrylate which contains trimethylammoniumethyl methacrylate in a range of about 1:20 relative to the neutral monomers wherein the ratio of copolymer a) to copolymer b) is 95:5.

9. A diltiazem formulation according to claim 8 wherein said delayed release diltiazem bead exhibits the following in-vitro dissolution profile in 0.1N HCl:
  a) from 0-5% of total diltiazem is released after 6 hours of measurement in said apparatus,
  b) from 0-10% of total diltiazem is released after 12 hours of measurement in said apparatus,
  c) from 0-35% of total diltiazem is released after 18 hours of measurement in said apparatus, and,
  d) from 50-90% of total diltiazem is released after 24 hours of measurement in said apparatus.

10. A diltiazem formulation according to claim 1 in which said rapid release diltiazem bead exhibits the following dissolution rate:
  a) from 0-20% of total diltiazem is released after 3 hours of measurement in said apparatus, and;
  b) from not less than 50% of total diltiazem is released after 6 hours of measurement in said apparatus.

11. A diltiazem formulation according to claim 10 in which said first polymeric coating of said rapid release diltiazem bead contains
  a) a copolymer of ethyl acrylate and methyl methacrylate which contains trimethylammoniumethyl methacrylate in a range of about 1:40 relative to the neutral monomers and
  b) a copolymer of ethyl acrylate and methyl methacrylate which contains trimethylammoniumethyl methacrylate in a range of about 1:20 relative to the neutral monomers wherein the ratio of copolymer a) to copolymer b) is 95:5.

12. A diltiazem formulation according to claim 11 wherein said first polymeric coating comprises from 10-15 w/w % of the total weight of a dried rapid release diltiazem bead.

13. A diltiazem formulation according to claim 1 wherein said blend exhibits the following in-vitro dissolution profile:
  a) from 25-40% of total diltiazem is released after 6 hours of measurement in said apparatus;
  b) from 30-45% of total diltiazem is released after 12 hours of measurement in said apparatus;
  c) from 40-65% of total diltiazem is released after 18 hours of measurement in said apparatus; and
  d) not less than 75% of total diltiazem is released after 24 hours of measurement in said apparatus.

* * * * *